United States Patent [19]

Bouwstra

[11] Patent Number: 5,830,499
[45] Date of Patent: Nov. 3, 1998

[54] PHOSPHOLIPID-AND CHOLESTROL-FREE AQUEOUS COMPOSITION FOR TOPICAL APPLICATION TO THE SKIN

[75] Inventor: Johanna Aaltje Bouwstra, Barendrecht, Netherlands

[73] Assignee: Rijksuniversiteit Leiden, Av Leiden, Netherlands

[21] Appl. No.: 809,667

[22] PCT Filed: Sep. 27, 1995

[86] PCT No.: PCT/NL95/00325

§ 371 Date: May 28, 1997

§ 102(e) Date: May 28, 1997

[87] PCT Pub. No.: WO96/09812

PCT Pub. Date: Apr. 4, 1996

[30] Foreign Application Priority Data

Sep. 27, 1994 [EP] European Pat. Off. ............... 94202783

[51] Int. Cl.⁶ .................................................. A61K 9/127
[52] U.S. Cl. .................... 424/450; 424/1.21; 424/78.03; 514/887
[58] Field of Search ................................ 424/450, 78.03, 424/1.21; 514/887

[56] References Cited

U.S. PATENT DOCUMENTS

| 3,957,971 | 5/1976 | Oleniacz | 424/450 |
| 4,536,324 | 8/1985 | Fujiwara et al. | 264/4.1 X |
| 4,673,567 | 6/1987 | Jizomoto | 424/450 |
| 5,021,200 | 6/1991 | Vanlerberghe et al. | 264/4.3 |
| 5,034,228 | 7/1991 | Meybeck et al. | 424/450 X |
| 5,091,111 | 2/1992 | Neumiller | 424/450 X |

FOREIGN PATENT DOCUMENTS

| 2090137 | 8/1993 | Canada . |
| 0 155 625 | 9/1985 | European Pat. Off. . |
| 0 557 825 | 9/1993 | European Pat. Off. . |
| 2 315 991 | 1/1977 | France . |
| 93/05767 | 4/1993 | WIPO . |
| 95/13052 | 5/1995 | WIPO . |
| 95/16436 | 6/1995 | WIPO . |

*Primary Examiner*—Richard D. Lovering
*Attorney, Agent, or Firm*—Browdy and Neimark

[57] ABSTRACT

Phospholipid- and cholesterol-free aqueous compositions for topical application to the skin contain a pharmaceutically active ingredient and a vector system of controlled and in-depth transport and release of the active ingredient through the skin. The vector system comprises at least one first non-ionic surfactant which forms vesicles upon dispersion in water and a lamellar phase upon concentrating the vesicles, and at least one second non-ionic hydrophilic surfactant. The ratios of the two non-ionic surfactants are such that the vector system comprises flexible vesicles.

17 Claims, 3 Drawing Sheets

PHOSPHOLIPID-AND CHOLESTROL-FREE AQUEOUS COMPOSITION FOR TOPICAL APPLICATION TO THE SKIN

CROSS-REFERENCE TO RELATED APPLICATIONS

This application is a 371 of PCT/NL95/00325, filed Sep. 27, 1995, based on EPO 94 202783.0, filed Sep. 27, 1994.

FIELD OF THE INVENTION

The present invention relates to aqueous compositions, containing a pharmaceutically active principle and a vector system consisting of a mixture of non-ionic surfactants in the form of vesicles having a particle size between 10 and 1000 nm, for application to the skin.

BACKGROUND OF THE INVENTION

Aqueous compositions containing one or more non-ionic surfactants in the form of vesicles have been known for a long time (see e.g. FR-2315991, published in 1977). From the many scientific articles and patent publications, which were published since, it will be readily appreciated by a person of ordinary skill in the art that lipids, and in particular phospholipids and/or cholesterol, and stabilisers, such as sodium lauryl sulphate, have to be added to such aqueous compositions containing non-ionic surfactant(s) in order to prevent coalescence, aggregation, sedimentation and phase transitions, e.g. to a micellar phase.

However, phospholipids and cholesterol appeared to have some disadvantages when incorporated in compositions, which are intended to be marketed and, thus, have to meet certain standards. It is known that phospholipids are not stable on storage at ambient conditions. Special measures are required to protect said compounds against degradation by light and/or oxygen. Another disadvantage of phospholipids is that—as naturally occurring products—they are mixtures of ester compounds. The composition of the phospholipids may, thus, vary from batch to batch and from source to source. It is also known that cholesterol can be easily oxidised in the presence of light. Autooxidation may also occur. Although the compound is a naturally occurring compound, also in human beings, many efforts are directed to a limitation of the uptake of externally administered cholesterol.

Therefore, there is a need to prevent the use of phospholipids and cholesterol in aqueous compositions, comprising one or more non-ionic surfactants in the form of vesicles and further containing a drug, for application to the skin.

SUMMARY OF THE INVENTION

The invention relates to a phospholipid- and cholesterol-free aqueous composition for topical application to the skin comprising a pharmaceutically active principle and a vector system for the controlled and in-depth transport and release of said active principle through skin layers, said vector system consisting of at least one first, non-ionic surfactant, forming vesicles upon dispersion in water and a lamellar phase upon concentrating said vesicles, and at least one second, non-ionic, hydrophilic surfactant, the ratio of said at least one first, non-ionic surfactant and said at least one second, non-ionic surfactant being such that the vector system consists of flexible vesicles. Upon lowering the water concentration of the composition a lamellar phase is formed close to a cubic, hexagonal or viscous isotropic phase boundary.

The vesicles of the present invention have a particle size of from 10 to 1000 nm.

DETAILED DESCRIPTION OF THE INVENTION

It has been found that aqueous dispersions of vesicles can be made from a mixture of at least two non-ionic surfactants without using phospholipids and/or cholesterol and derivatives thereof, provided that at least one of the non-ionic surfactants can intrinsically form vesicles when dispersed in water and a lamellar phase upon concentrating said dispersion of vesicles at room temperature. The second surfactant is a hydrophilic surfactant and is not able to intrinsically form vesicles when dispersed in water. The HLB-value for the second surfactant is at least 12. In the final composition, comprising a medicament and the said mixture of non-ionic surfactants in water, vesicles are also present and upon lowering the water concentration of the composition a lamellar phase is formed which is close to a cubic, hexagonal or viscous isotropic phase boundary, mainly dependent of the non ionic surfactant(s) used in the mixture.

The non-ionic surfactants, which have appeared to be useful as the lamellar layer forming surfactant on the one hand and as the second surfactant on the other hand, are preferably selected from the group consisting of polyoxyethylene alkyl ethers and esters (hereafter referred to as POE-alkyl ethers and esters) sorbitan esters, glucose esters and sucrose alkyl esters. Examples thereof are listed in the tables below.

TABLE I

LAMELLAR LAYER FORMING SURFACTANTS

| Code/tradename | Official name | HLB | Supplier |
| --- | --- | --- | --- |
| L-595 | sucrose laurate ester (30% mono, 70% di/tri/poly) | 5 | Ryoto |
| Tween ® 81 | POE(5) sorbitan monooleate | 10.0 | ICI |
| Tween ® 85 | POE(2) sorbitan trioleate | 11.0 | ICI |
| Span ® 20 | sorbitan mono laurate | 8.6 | Sigma |
| Span ® 80 | sorbitan mono oleate | 4.3 | ICI |
| Span ® 85 | sorbitan trioleate | 1.8 | Sigma |
| Gluc D.O. | dioleyl glucate | | Amerchol |
| $C_{12}EO_3$ | POE(3) dodecylether | 9.4 | Servo, Delden |
| Serdox NOG ® S-200 | POE(4.5) oleylester | 8.7 | Servo, Delden |

TABLE II

SECOND SURFACTANT

| Code/tradename | Official name | HLB | Supplier |
| --- | --- | --- | --- |
| $C_{12}EO_7$ | POE(7) dodecylether | 12.9 | Servo, Delden |
| Brij ® 96 | POE(10)-oleylether | 12.4 | ICI |
| L-1695 | Sucrose laurate | 16 | Ryoto |
| PEG-8-laurate | POE(8) dodecylester | 13.5 | Diopeg |
| Serdox NOG ® S-440 | POE(10) oleylester | 12.4 | Servo, Delden |

Also mixtures of representatives of these groups may be used.

The mean degree of polymerisation of the POE-alkyl ethers and esters may range from 2 to 30 and preferably from 2 to 10. The number of alkyl chains is 1 or 2 for the POE-alkyl ethers and esters and-one or more for the sucrose alkyl esters. The number of carbon atoms in the alkyl chain(s) of all non-ionic surfactants belonging to the above-mentioned group may range from 8 to 30 and preferably from 12 to 17. The alkyl chain(s) may be straight or branched, saturated or unsaturated. In case of a saturated alkyl chain there is a preference for 1-dodecyl (lauryl). In case of an unsaturated alkyl chain there is a preference for oleyl.

The total concentration of non-ionic surfactants may be up to 15 wt %, the percentage being based on the weight of the composition. However, it is preferred to use concentrations up to 7.5 wt % and more preferably up to 5 wt %.

The particle size of the vesicles may range from 10 to 1000 nm, but for particle sizes ranging from 50 to 500 nm are preferred. A particle size from 100 to about 250 nm however is most preferred. By extruding the dispersion of vesicles through a membrane, having a pore size of $\leq \frac{1}{3}*$ vesicle diameter, the mean particle size of the vesicles in general is not changed.

In view of the stability of the vesicles it is important that after extrusion the dispersion still be homogeneous, a measure for the homogeneity being the polydispersity index as measured by means of a dynamic light scattering apparatus.

The ratio of the non-ionic surfactant(s), intrinsically forming vesicles when dispersed in water, to the non-ionic surfactant(s), not forming vesicles in water, may vary according to the surfactants and the drug used. However, it should be stressed that it is important that the final composition still contain vesicles, because of the possibilities for encapsulating a drug into the vesicles.

To the compositions according to the present invention an ionic surfactant as a stabiliser may occasionally be added. Examples thereof are sodium laurate and sodium dicetyl phosphate.

The present vesicles may also contain a fatty alcohol, specifically a $C_{15}$–$C_{25}$ fatty alcohol, preferably a $C_{20}$–$C_{24}$ fatty alcohol. Since the said compounds are well-known as thickening agents and/or as co-emulsifiers in the preparation of solid and semi-solid fatty compositions such as sticks, creams and ointments, it is surprising that the addition of the fatty alcohols to the vesicles of the present invention, does not have a negative impact on the extrudability and mean particle size as compared with those of the vesicles not containing a fatty alcohol.

The drug in the compositions according to the present invention may be encapsulated in the vesicles, may adhere to the vesicles or may be located in the aqueous continuous phase. It will be readily understood that there is an upper limit to the amount of drug that can be encapsulated into the vesicles and that the ratio of encapsulated drug to not-encapsulated drug depends on the concentration and composition of the vesicles and the properties of the drug.

The aqueous compositions containing a mixture of non-ionic surfactants in the form of vesicles can be prepared according to methods as known in the art of liposome and niosome technology.

The compositions according to the present invention are applied to the skin in order to deliver the medicament incorporated therein to the place where the therapeutical action is required or can become effective. Advantageously the compositions of the present invention can be used for intradermal as well as for transdermal administration of drugs.

Biodistribution studies performed with several dispersions of vesicles according to the present invention and a prior art composition containing rigid vesicles (composition III in Example 9) clearly demonstrate that the dispersions containing flexible vesicles penetrate into the skin faster, deeper and to a greater extent than the prior art dispersion (see also FIG. 1, tables III–VI).

The composition containing a fatty alcohol (composition IV) in addition thereto penetrates into the skin faster, deeper and to a greater extent than the corresponding composition not containing such a fatty alcohol (composition I, tables III–VI, FIG. 1).

From FIG. 2 it clearly appears that the $^{14}$C-label apparently penetrates into the skin at a lower rate than the $^{3}$H-label (see also tables III to VII).

The compositions according to the present invention offer interesting possibilities for pharmaceutical product development.

Vesicles can be prepared without being forced to use phospholipids and/or cholesterol which have appeared to be broken down on storage and adversely affect the stability of the vesicles.

In the second place there is only a limited amount of non-ionic surfactants that have the intrinsic property of forming vesicles when dispersed in water and a lamellar phase upon concentrating said vesicles. By mixing a non-ionic surfactant which is able to do so with one or more non-ionic surfactants, which intrinsically do not form vesicles when dispersed in water and a lamellar phase upon lowering the water concentration but a cubic, hexagonal or viscous isotropic phase on dispersion in water, the scope of surfactants that can be used in product development is widely broadened.

Furthermore, by using a mixture of non-ionic surfactants and varying the ratio of the components, the properties of the vesicles can be changed in order to comply with the standards set for the final product, e.g. with respect to the amount of encapsulated drug, rate of release of the drug from the vesicles.

Although the foregoing invention has been described in some detail by way of illustration and example for purposes of clarity and understanding, it will be readily apparent to those of ordinary skill in the art in the light of the teachings of this invention that certain changes and modifications may be made thereto without departing from the spirit and the scope of the appended claims.

BRIEF DESCRIPTION OF THE DRAWINGS

The following examples and accompanying figures illustrate the invention.

EXAMPLES

Example 1

Figure 1:
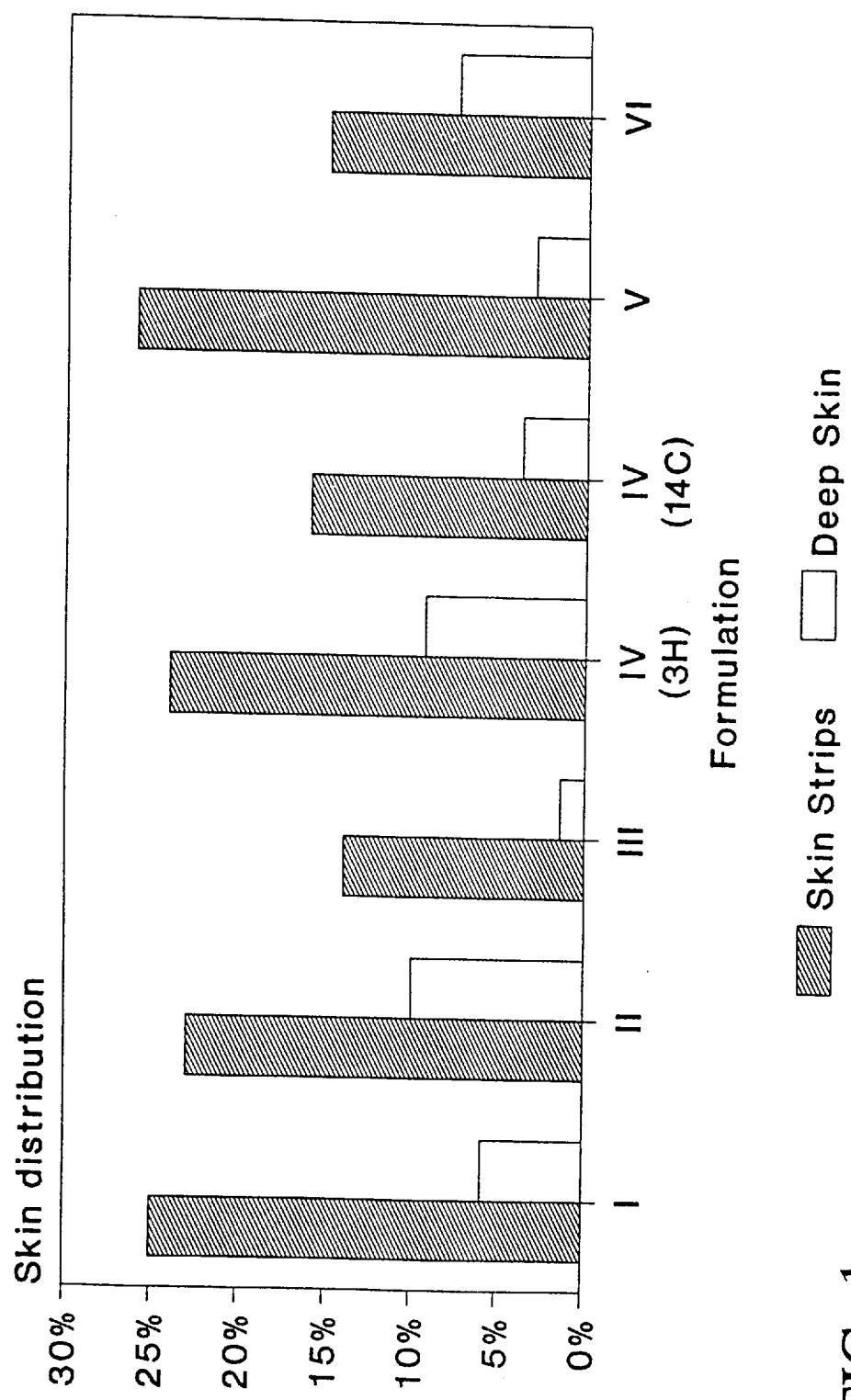
FIG. 1 shows the distribution of radio-activity recovered from the skin, 6 h after dermal application of several formulations.

A mixture of non-ionic surfactants (see the tables for the composition; the weight ratio of the surfactants used is based on their molecular weights) in an amount required to obtain a final aqueous dispersion containing 5 wt % was dissolved in about 2 ml of a mixture of chloroform/ methanol (3/1) in a test tube. The mixture of organic solvents was subsequently evaporated by means of overnight vacuum centrifugation. The remaining dry film in the test tube was hydrated by adding 5 ml of Phosphate Buffered Saline (PBS; pH of 7.4). The tube was placed in a water bath of 8° C. for 10 minutes. Thereafter the dispersion was sonicated at 80° C. for 45 seconds. After cooling the dispersion to room temperature, the same was extruded using an extruder (Sartorius), equipped with an extrusion membrane (pore size 200 nm; Nuclepore) and operated under nitrogen pressure of about 1–1.5 bar. By means of polarised light microscopy and dynamic light scattering the presence of vesicles was assessed and the mean particle size thereof determined.

Mixtures of POE(3)-dodecyl ether (=$C_{12}EO_3$) and POE(7)-dodecyl ether (=$C_{12}EO_7$)

| ratio $C_{12}EO_3$:$C_{12}EO_7$ | stable dispersion of vesicles | mean particle size of vesicles (nm) |
|---|---|---|
| 0.9:0.1 | yes | 166, 167 |
| 0.8:0.2 | yes | 157 |
| 0.7:0.3 | yes | 151, 126 |
| 0.6:0.4 | yes | 177, 184 |
| 0.5:0.5 | yes | 164, 149, 182 |
| 0.4:0.6 | yes | 167, 186 |
| 0.3:0.7 | yes | 101, 189 |

Mixtures of sucrose laurate ester (Ryoto L-595) and POE(7)-dodecyl ether (=$C_{12}EO_7$)

| ratio Ryoto L-595: $C_{12}EO_7$ | stable dispersion of vesicles | mean particle size of vesicles (nm) |
|---|---|---|
| 0.3:0.7 | yes | 132, 142, 138, 138 |
| 0.2:0.8 | yes | 139, 130, 135, 142, 132, 143 |
| 0.1:0.9 | yes | 110, 141, 84 |

Mixtures of POE(4.5)-oleyl ester (=S-200) and POE(10)-oleyl ester (=S-440)

| ratio S-200:S-440 | stable dispersion of vesicles | mean particle size of vesicles (nm) |
|---|---|---|
| 0.6:0.4 | yes | 288 |
| 0.5:0.5 | yes | 223 |
| 0.4:0.6 | yes | 183 |
| 0.3:0.7 | yes | 155, 155 |
| 0.2:0.8 | yes | 144, 136, 135 |
| 0.1:0.9 | yes | 120, 114 |

Example 2

The experiments as described under Example 1 were repeated, but the vesicles-containing dispersions, after extrusion through a 200 nm pore size membrane were additionally extruded using the same extruder (Sartorius), equipped with an extrusion membrane (pore size 30 nm; Nuclepore) and operated under nitrogen pressure of about 4 bar. The mean particle size of the vesicles and polydispersity index after extrusion through the first membrane and through the second membrane were determined, by dynamic light scattering (DLS) at 25° C. with a Malvern 4700 system using a 25 mW He—Ne laser (NEC, Tokyo, Japan) and the automeasure version 3.2 software (Malvern Ltd., Malvern, UK). For viscosity and refractive index values of the water were used. The system reports a polydispersity index as a measure of the particle size distribution. This index ranges from 0.0 for an entirely homogeneous dispersion up to 1.0 for a dispersion with a completely heterogeneous size distribution.

Mixtures of POE(3)-dodecyl ether (=$C_{12}EO_3$) and POE(7)-dodecyl ether (=$C_{12}EO_7$)

| | mean particle size (nm) of vesicles after extrusion through: (polydispersity index between brackets) | |
|---|---|---|
| ratio $C_{12}EO_3$:$C_{12}EO_7$ | 200 nm pore size membrane | 30 nm pore size membrane |
| 0.9:0.1 | 139(0.19), 153(0.13) | 139(0.32), 156(0.31) |
| 0.8:0.2 | 145(0.13), 148(0.16) | 97(0.25), 78(0.22) |
| 0.7:0.3 | 136(0.19), 126(0.19) | 110(0.34) 77.3(0.22) |
| 0.6:0.4 | 184(0.15), 165(0.11), 204(0.15) | 204(0.21), 185(0.14), 188(0.21) |
| 0.5:0.5 | 198(0.13), 182(0.15), 172(0.13), 192(0.14) | 168(0.15), 176(0.16), 183(0.14), 186(0.15) |
| 0.4:0.6 | 167(0.15), 186(0.15), 165(0.15), 193(0.15) | 172(0.11), 176(0.19), 251(0.38), 190(0.20) |
| 0.3:0.7 | 189(0.25) | 128(0.30) |

Mixtures of sucrose laurate ester (Ryoto L-595) and POE(7)-dodecyl ether (=$C_{12}EO_7$)

| | mean particle size (nm) of vesicles after extrusion through: (polydispersity index between brackets) | |
|---|---|---|
| ratio Ryoto L-595:$C_{12}EO_7$ | 200 nm pore size membrane | 30 nm pore size membrane |
| 0.3:0.7 | 142(0.10), 138(0.09), 138(0.14) | 119(0.11), 137(0.07), 121(0.10) |
| 0.2:0.8 | 151(0.12), 138(0.12), 142(0.07), 132(0.11), 143(0.12) | 161(0.19), 157(0.17), 134(0.15), 147(0.21), 132(0.18) |
| 0.1:0.9 | 83.5(0.36) | 141(0.30) |

Mixtures of POE(4.5)-oleyl ester (=S-200) and POE(10)-oleyl ester (=S-440)

| | mean particle size (nm) of vesicles after extrusion through: (polydispersity index between brackets) | |
|---|---|---|
| ratio S-200: S-440 | 200 nm pore size membrane | 30 nm pore size membrane |
| 0.3:0.7 | 155(0.24), 155(0.25) | 88.1(0.21), 86.3(0.20) |
| 0.2:0.8 | 136(0.25), 135(0.25) | 76.0(0.19), 75.1(0.20) |
| 0.1:0.9 | 120(0.23), 114(0.23) | 68.8(0.19), 68.0(0.16) |

Example 3

Experiments were performed as described under example 2 using $C_{12}EO_7$ as the second surfactant. The dispersion after extruding through the first membrane (200 nm pore size) was extruded through a second membrane having a pore size of either 30 nm or 50 nm. The extrusion rate (mg/min.) is determined by dividing the amount of dispersion of vesicles, extruded through the extruding membrane for a period of 3 to 10 min. after the first droplets were extruded, by the said period. The total amount of dispersion extruded is about 1 to 1,5 ml.

| $C_{12}EO_7$ | L-595 | Vesicles | extrudability |
|---|---|---|---|
| 4 | 6 | +/− | +/− |
| 3 | 7 | + | + |
| 2 | 8 | + | + |

| $C_{12}EO_7$ | Tween® 81 | Vesicles | extrudability |
|---|---|---|---|
| 6 | 4 | +/− | + |
| 4 | 6 | + | + |
| 2 | 8 | + | + |
| 1 | 9 | +/− | + |
| 0.5 | 9.5 | +/− | + |

| $C_{12}EO_7$ | Tween® 85 | Vesicles | extrudability |
|---|---|---|---|
| 4 | 6 | + | + |
| 2 | 8 | + | + |
| 0 | 10 | + | + |

| $C_{12}EO_7$ | Span® 20 | Vesicles | extrudability |
|---|---|---|---|
| 6 | 4 | +/− | + |

| $C_{12}EO_7$ | Span® 80 | Vesicles | extrudability |
|---|---|---|---|
| 6 | 4 | +/− | + |
| 4 | 6 | +/− | + |

| $C_{12}EO_7$ | Gluc D.O. | Vesicles | extrudability |
|---|---|---|---|
| 6 | 4 | +/− | + |
| 4 | 6 | +/− | + |

Vesicles
+ : vesicles present; +/− : vesicles and spheres
Extrudability
+ : extrusion through 30 nm pore size membrane or extrusion through 50 nm pore size membrane (>1000 mg/min)
+/− : extrusion through 50 nm pore size (100–1000 mg/min)

Example 4

Experiments were performed as described under example 2 using Brij® 96 as the second surfactant. The dispersion after extruding through the first membrane (200 nm pore size) was extruded through a second membrane having a pore size of either 30 nm or 50 nm.

| Brij® 96 | Tween® 85 | Vesicles | extrudability |
|---|---|---|---|
| 6 | 4 | +/− | + |
| 4 | 6 | + | + |
| 2 | 8 | + | + |
| 0 | 10 | + | + |

| Brij® 96 | Span® 20 | Vesicles | extrudability |
|---|---|---|---|
| 4 | 6 | +/− | + |

| Brij® 96 | Span® 85 | Vesicles | extrudability |
|---|---|---|---|
| 4 | 6 | +/− | +/− |

For the meaning of the symbols see example 3

Example 5

Experiments were performed as described under example 2 using. L-1695 as the second surfactant. The dispersion after extruding through the first membrane (200 nm pore size) was extruded through a second membrane having a pore size of either 30 nm or 50 nm.

| L-1695 | L-595 | Vesicles | extrudability |
|---|---|---|---|
| 6 | 4 | + | + |
| 4 | 6 | + | + |
| 2 | 8 | + | + |
| 3 | 7 | + | + |

| L-595 | PEG-8 laurate | Vesicles | extrudability |
|---|---|---|---|
| 7 | 3 | + | + |
| 9 | 1 | + | +/− |

For the meaning of the symbols see example 3

Example 6

A dispersion of vesicles was prepared using L-595 as the lamellar layer forming surfactant, L-1695 as the second surfactant and dicetyl phosphate as a stabiliser in a molecular weight ratio of 5.875:3.875:0.25. The dispersion of vesicles could be extruded through a 30 nm pore size membrane.

Example 7

Tween® 81 and L-595 (lamellar layer forming surfactants) and $C_{12}EO_7$ (second surfactant) in a molecular weight ratio of 9.5:2:0.5 were dispersed in water. Both vesicles and spheres could be observed by means of a polarised light microscope. The dispersion could be extruded through a 30 nm pore size membrane.

Example 8

The manufacturing method of example 1 was followed, but now 2.5% of 1-docosanol was added to the solution of surfactants in the mixture of chloroform/methanol. The combinations of non-ionic surfactants used were:
1. $C_{12}EO_7$: L-595 (3:7)
2. L-1695: L-595 (4:6)
3. PEG(8) laurate: L-595 (7:3).
4. Also 1-docosanol was incorporated in vesicles consisting of L-1695, L-595 and dicetyl phosphate in a molecular weight ratio of 3:7:0.1.

The dispersions of vesicles nos 1 and 3 containing 1-docosanol had the same characteristics as the vesicles without containing 1-docosanol. Incorporating 1-docosanol in the composition no. 2 had a negative impact. By the addition of the stabiliser dicetyl phosphate (composition no. 4) a dispersion of vesicles could be obtained, the vesicles having a diameter slightly greater than those without containing 1-docosanol.

Example 9

Biodistribution Studies of Topically Applied Compositions According to the Present Invention Materials Non-ionic surfactants were obtained from the companies as specified in the tables I and II. Cholesterol and dicetyl phosphate were supplied by Sigma Chemicals (St. Louis, Mo., USA). [$1\alpha$, $2\alpha(n)$-$^3$H]cholesteryl oleoyl ether (spec. act. 1.71 TBq/mmol) was supplied by Amersham (Buckinghamshire, UK). Hionic Fluor, Plasmasol and Soluene-350 were purchased from Packard Instruments (Downers Grove, Ill., USA). All other reagents were of analytical grade.

Preparation of [$^3$H]-Labelled Vesicles

Vesicles were composed of a mixture of several non-ionic surfactants. [$^3$H]-cholesteryl oleoyl ether was added as a radioactive marker. In general, 25 mg of non-ionic surfactants and [$^3$H]-cholesteryl oleoyl ether were dissolved in a mixture of chloroform/ methanol (3:1) v/v) and evaporated to dryness under $N_2$ for at least 90 min. The film was hydrated in 500 µl sterile PBS (3.6 mM $KH_2PO_4$, 6.4 mM $NaH_2PO_4$, 145 mM NaCl, pH 7.4) or in a sterile phosphate buffered glucose solution. The resulting dispersion was subsequently sonicated preferably until a mean particle size between 100 and 150 nm was obtained.

Preparation of [$^3$H]- and [$^{14}$C]-Labelled Vesicles

Vesicles were prepared of a mixture of L-595 and $C_{12}EO_7$ as described under previous paragraph, but now docosanol and [$^{14}$C]-labelled docosanol were added in such an amount that the vesicles contained about 7*10$^3$ mol. % [$^3$H]-cholesteryl oleoylether and a mixture of docosanol and [$^{11}$C]-labelled docosanol (composition IV, table III).

Animals

Wistar rats (U:WU,CPB) with an average weight of 240–260 g from the animal facility of the University of Utrecht were used. Animals received standard laboratory chow and water ad libitum.

Animal Experiments

Prior to application of vesicles, rats were injected i.p. with a mixture of ketamine, xylazine and atropine (KRA). Subsequently, hair of the lower part of the neck/upper part of the back was clipped. 24 hours after clipping of the hair, [$^3$H]-labelled vesicles were applied to 1 cm$^2$ of clipped skin of rats under KRA anaesthesia. The amount of surfactant per application was 1 mg in a volume of 20 µl.

At 6, 24, 48 and occasionally 96 hours post-application rats were anaesthetised with ether. Rats were then killed by cervical dislocation. Subsequently the site of application as well as surrounding tissue was wiped twice with a water wetted swab and once with a dry swab. Then the site of application was stripped 20 times with tape. Finally, remaining skin was excised and radioactivity in swabs, each strip and skin was determined.

Radioactivity Measurements

Radioactivity in swabs and strips was determined by adding 10 ml of Hionic and warming the samples overnight at 40° C.

Radioactivity in remaining skin at the site of application was determined by dissolving the skin completely in respectively 7, 3 and 1 ml of Soluene-350. To 750 µl of dissolved skin 10 ml of Hionic was added. Radioactivity was assayed with 10 ml of Hionic as a scintillation fluid.

Figure 2:
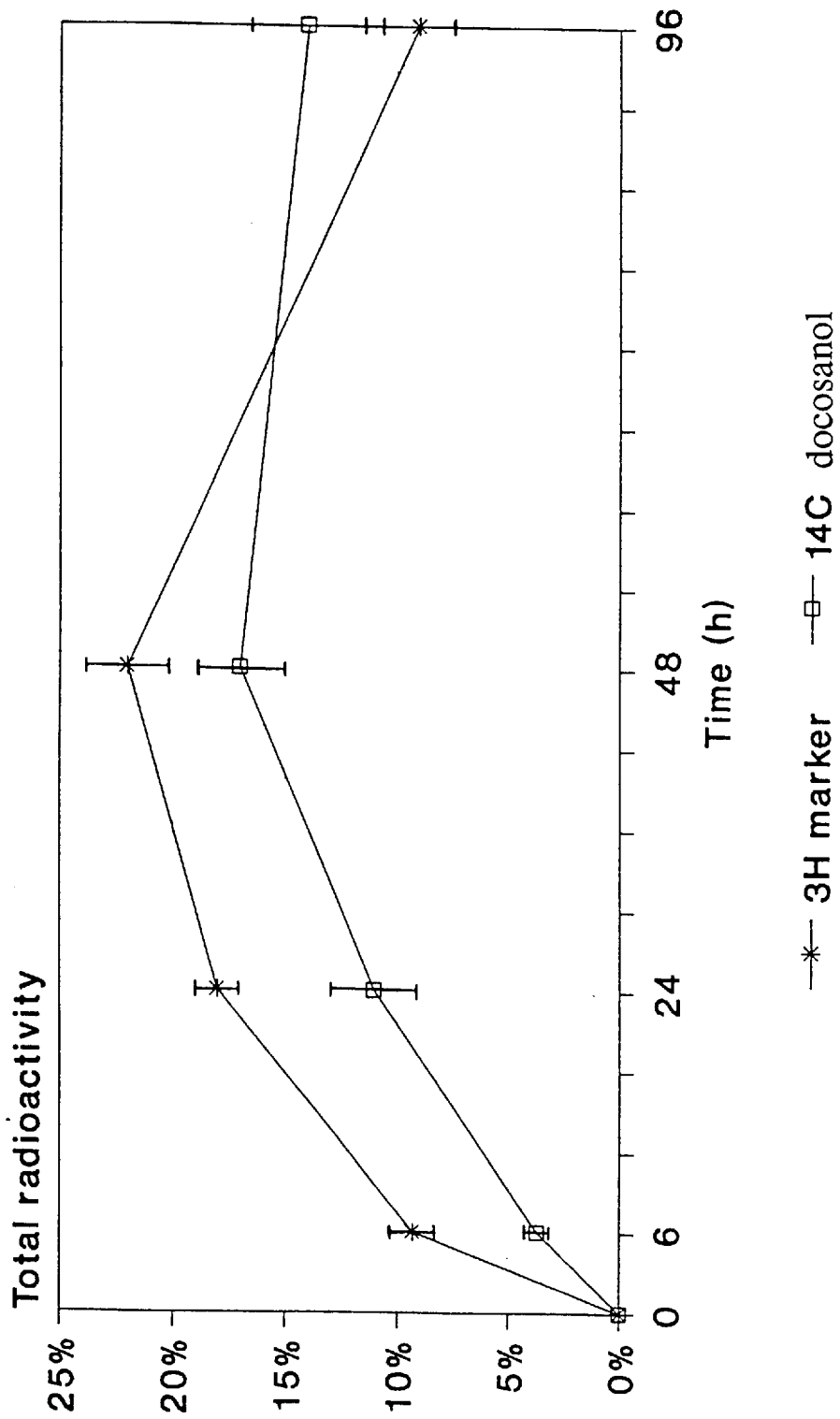
FIG. 2 shows the percentage radio-activity in deep skin after application of formulation IV.
Figure 3:
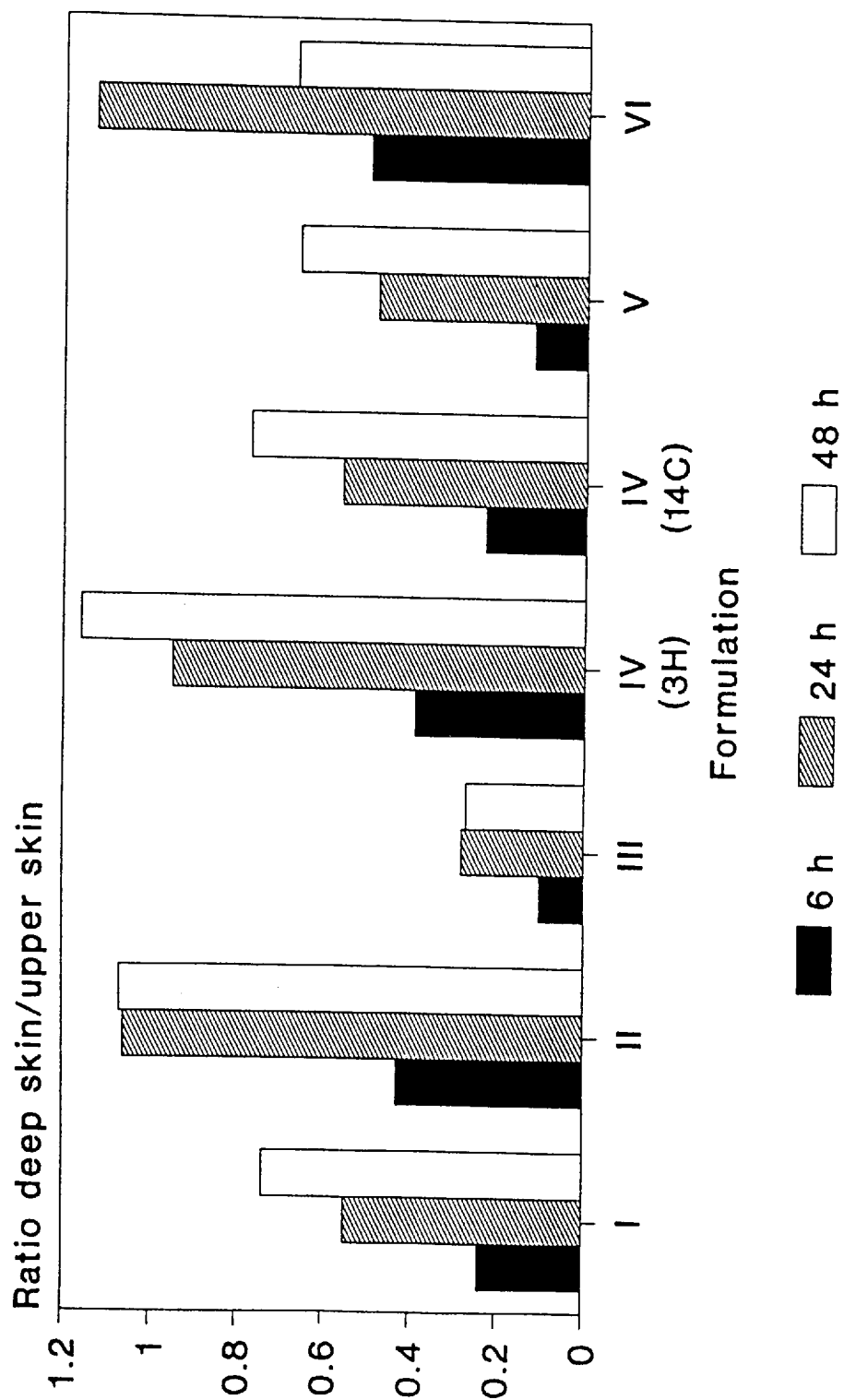
FIG. 3 shows the ratio deep skin/upper skin recovered at 6,24 and 48 h after dermal application of several formulations.

The results of the above tests are given in tables IV to VII and FIGS. 1, 2 and 3.

TABLE III–VII

TABLE III

Vesicles-containing preparations as used in the biodistribution studies

| | composition[1] | dose | size (nm) | pd | remarks |
|---|---|---|---|---|---|
| I | L595:$C_{12}EO_7$ (7:3) | 1 mg = 20 µl | 119 | 0.33 | |
| II | L595:PEG8-laurate (7:3) | 1 mg = 20 µl | 119 | 0.31 | |
| III | WASAG7:Chol:DCP (5:4:1) | 1 mg = 20 µl | 109 | 0.35 | |
| IV | L595:$C_{12}EO_7$:docosanol[2] (7:3:0.1) | 1 mg = 20 µl | 126 | 0.33 | |
| V | L595:L1695:DCP (7:3:0.1) | 1 mg = 20 µl | 196 | 0.14 | a phosphate buffered glucose solution was chosen as hydration medium |
| VI | $C_{12}EO_7$:Tween ® 81 (1:9) | 1 mg = 20 µl | 158 | 0.19 | a phosphate buffered glucose solution was chosen as hydration medium |

[1]vesicles contained about 1*10$^3$ mol % [$^3$H]-cholesteryloleoylether
[2]vesicles contained about 7*10$^3$ mol % [$^3$H]-cholesteryloleoylether and a mixture of docosanol and $^{14}$C-labeled docosanol

TABLE IV

Biodistribution as percentage of dose radioactivity 6 h after application

| | vesicles[1] | label | swabs | strips | deep skin[2] | total[3] |
|---|---|---|---|---|---|---|
| I | L595:$C_{12}EO_7$ | $^3$H | 67 (±4) | 25 (±5) | 5.9 (±1.5) | 98 (±2) |
| II | L595:PEG8-laurate | $^3$H | 61 (±3) | 23 (±3) | 10 (±0.1) | 93 (±3) |
| III | WASAG7:Chol:DCP | $^3$H | 86 (±3) | 14 (±2) | 1.4 (±0.4) | 101 (±0.2) |
| IV | L595:$C_{12}EO_7$:docosanol | $^3$H | 61 (±4) | 24 (±5) | 9.3 (±1.1) | 95 (±2) |
| | | $^{14}$C | 85 (±4) | 16 (±2) | 3.7 (±0.5) | 105 (±4) |
| | | ratio[4] $^3$H/$^{14}$C | 0.72 (±0.03) | 1.45 (±0.21) | 2.51 (±0.46) | 0.90 (±0.02) |
| V | L595:L1695:DCP | $^3$H | 71 (±2) | 26 (±2) | 3.0 (±0.7) | 100 (±1) |

TABLE IV-continued

Biodistribution as percentage of dose radioactivity 6 h after application

| vesicles[1] | label | swabs | strips | deep skin[2] | total[3] |
|---|---|---|---|---|---|
| VI $C_{12}E0_7$:Tween ® 81 | $^3H$ | 62 (±2) | 15 (±3) | 7.5 (±1.1) | 85 (±3) |

[1]for detailed description see table III
[2]remaining skin at site of application after swabs and strips
[3]total amount recovered from strips, swabs and remaining skin
[4]ratio $^3H/^{14}C$ calculated as percentage of dose $^3H$ divided by percentage of dose $^{14}C$ recovered

TABLE V

Biodistribution as percentage of dose radioactivity 24 h after application

| | vesicles[1] | label | swabs | strips | deep skin[2] | total[3] |
|---|---|---|---|---|---|---|
| I | L595:$C_{12}E0_7$ | $^3H$ | 40 (±7) | 22 (±4) | 12 (±1) | 73 (±11) |
| II | L595:PEG8-laurate | $^3H$ | 45 (±2) | 17 (±3) | 18 (±3) | 80 (±2) |
| III | WASAG7:Chol:DCP | $^3H$ | 45 (±15) | 18 (±2) | 5 (±1) | 67 (±14) |
| IV | L595:$C_{12}E0_7$:docosanol | $^3H$ | 51 (±4) | 19 (±3) | 18 (±1) | 88 (±4) |
| | | $^{14}C$ | 66 (±7) | 19 (±1) | 11 (±2) | 97 (±4) |
| | | ratio[4] $^3H/^{14}C$ | 0.77 (±0.06) | 1.04 (±0.23) | 1.58 (±0.25) | 0.91 (±0.01) |
| V | L595:L1695:DCP | $^3H$ | 52 (±4) | 27 (±2) | 13 (±4) | 93 (±0.5) |
| VI | $C_{12}E0_7$:Tween ® 81 | $^3H$ | 32 (±5) | 15 (±0.4) | 17 (±2) | 64 (±4) |

[1]for detailed description see table III
[2]remaining skin at site of application after swabs and strips
[3]total amount recovered from strips, swabs and remaining skin
[4]ratio $^3H/^{14}C$ calculated as percentage of dose $^3H$ divided by percentage of dose $^{14}C$ recovered

TABLE VI

Biodistribution as percentage of dose radioactivity 48 h after application

| | vesicles[1] | label | strips | deep skin[2] |
|---|---|---|---|---|
| I | L595:$C_{12}E0_7$ | $^3H$ | 19 (±3) | 14 (±2) |
| II | L595:PEG8-laurate | $^3H$ | 15 (±3) | 16 (±2) |
| III | WASAG7:Chol:DCP | $^3H$ | 15 (±2) | 4.1 (±1.2) |
| IV | L595:$C_{12}E0_7$:docosanol | $^3H$ | 19 (±3) | 22 (±2) |
| | | $^{14}C$ | 22 (±1.4) | 17 (±2) |
| | | ratio[3] $^3H/^{14}C$ | 0.87 (±0.06) | 1.32 (±0.11) |
| V | L595:L1695:DCP | $^3H$ | 20 (±1) | 12 (±3) |
| VI | $C_{12}E0_7$:Tween ® 81 | $^3H$ | 18 (±2) | 12 (±1) |

[1]for detailed description see table III
[2]remaining skin at site of application after swabs and strips
[3]ratio $^3H/^{14}C$ calculated as percentage of dose $^3H$ divided by percentage of dose $^{14}C$ recovered

TABLE VII

Biodistribution as percentage of dose radioactivity 96 h after application

| vesicles[1] | label | strips | deep skin[2] |
|---|---|---|---|
| L595:$C_{12}E0_7$:docosanol | $^3H$ | 21 (±5) | 9.0 (±2.1) |
| | $^{14}C$ | 23 (±4) | 14 (±3) |
| | ratio[3] $^3H/^{14}C$ | 0.91 (±0.15) | 0.65 (±0.03) |

[1]for detailed description see table III
[2]remaining skin at site of application after swabs and strips
[3]ratio $^3H/^{14}C$ calculated as percentage of dose $^3H$ divided by percentage of dose $^{14}C$ recovered

I claim:

1. Phospholipid- and cholesterol-free aqueous composition for topical application to the skin comprising a pharmaceutically active principle and a vector system for the controlled and in-depth transport and release of said active principle through skin layers, said vector system consisting of at least one first, non-ionic surfactant, said first non-ionic surfactant forming vesicles upon dispersion in water and a lamellar phase upon concentrating said vesicles, and at least one second, non-ionic, hydrophilic surfactant which does not intrinsically form vesicles when dispersed in water, the ratio of said at least one first, non-ionic surfactant and said at least one second, non-ionic surfactant being such that the vector system consists of flexible vesicles.

2. Aqueous composition according to claim 1, wherein upon lowering the water concentration of the composition a lamellar phase is formed close to a cubic, hexagonal or isotropic phase boundary.

3. Aqueous composition according to claim 1, wherein said vesicles have a particle size of from 10 to 1000 nm.

4. Aqueous composition according to claim 3 wherein said vesicles have a particle size of from 50 to 500 nm.

5. Aqueous composition according to one claim 1, wherein said flexible vesicles can be extruded through an extrusion membrane having pore sizes of about 20 to 70 nm.

6. Aqueous composition according to claim 5 wherein said flexible vesicles can be extruded through an extrusion membrane having pore sizes of about 30 to 50 nm.

7. Aqueous composition according to claim 1, wherein said second surfactant has an HLB value of at least 12.

8. Aqueous composition according to claim 1, wherein said non-ionic surfactants are selected from the group consisting of polyoxyethylene ethers, polyoxyethylene esters, sucrose esters, sorbitan esters and glucate esters.

9. Aqueous composition according to claim 1, wherein said first, non-ionic surfactant is selected from the group consisting of:
sucrose laurate ester (30% mono, 70% di/tri/poly),
POE(5) sorbitan monooleate,
POE(2) sorbitan trioleate,
sorbitan monolaurate,
sorbitan monooleate,
sorbitan trioleate,
dioleyl glucate,
POE(3) dodecyl ether and
POE(4,5) oleylester.

10. Aqueous composition according to claim 9, wherein said first non-ionic surfactant is selected from the group consisting of POE(3)-dodecyl ether, sucrose laurate ester, POE(5)-sorbitan mono-oleate, and POE(2)-sorbitan trioleate.

11. Aqueous composition according to claim 1, wherein said second non-ionic surfactant is selected from the group consisting of:
POE(7) dodecyl ether,
POE(10) oleylether,
POE(8) dodecylester,
POE(10) oleylester and
sucrose laurate.

12. Aqueous composition according to claim 11, wherein said second non-ionic surfactant is selected from the group consisting of POE(7)-dodecylether, sucrose laurate ester and POE(8)-dodecyl ester.

13. Aqueous composition according to claim 1, wherein said composition further comprises a stabiliser.

14. Aqueous composition according to claim 1, wherein the concentration of non-ionic surfactants amounts up to 15 wt % based on the weight of the composition.

15. Aqueous composition according claim 1, wherein said composition further comprises a $C_{15}$–$C_{25}$ fatty alcohol.

16. Aqueous composition according to claim 15, wherein said composition further comprises a $C_{20-24}$ fatty alcohol.

17. A composition for topical application to the skin comprising an effective amount of a medication that can be administered by intradermal and/or transdermal delivery to a patient in need therein and an aqueous composition according to claim 1.

* * * * *